United States Patent
Yamashita

(10) Patent No.: US 10,570,240 B2
(45) Date of Patent: Feb. 25, 2020

(54) ACTIVE ENERGY RAY-CURABLE COMPOSITION AND ANTISTATIC FILM

(71) Applicant: FUJIFILM Corporation, Tokyo (JP)

(72) Inventor: Masako Yamashita, Ashigara-kami-gun (JP)

(73) Assignee: FUJIFILM Corporation, Tokyo (JP)

( * ) Notice: Subject to any disclaimer, the term of this patent is extended or adjusted under 35 U.S.C. 154(b) by 136 days.

(21) Appl. No.: 15/464,567

(22) Filed: Mar. 21, 2017

(65) Prior Publication Data
US 2017/0190825 A1   Jul. 6, 2017

Related U.S. Application Data

(63) Continuation of application No. PCT/JP2015/075826, filed on Sep. 11, 2015.

(30) Foreign Application Priority Data

Sep. 29, 2014  (JP) ................ 2014-199083

(51) Int. Cl.
| | | |
|---|---|---|
| C08F 293/00 | (2006.01) | |
| C08F 265/06 | (2006.01) | |
| C08F 220/36 | (2006.01) | |
| C08F 2/00 | (2006.01) | |
| C08F 2/48 | (2006.01) | |
| C08J 7/04 | (2020.01) | |
| C07C 45/63 | (2006.01) | |
| C09D 4/06 | (2006.01) | |
| C07C 67/293 | (2006.01) | |
| C07C 67/08 | (2006.01) | |
| B05D 3/06 | (2006.01) | |
| C08F 220/28 | (2006.01) | |
| C08F 220/34 | (2006.01) | |
| C08F 226/02 | (2006.01) | |

(Continued)

(52) U.S. Cl.
CPC .............. *C08F 293/00* (2013.01); *B05D 3/06* (2013.01); *C07C 45/63* (2013.01); *C07C 67/08* (2013.01); *C07C 67/293* (2013.01); *C08F 2/005* (2013.01); *C08F 2/48* (2013.01); *C08F 220/28* (2013.01); *C08F 220/34* (2013.01); *C08F 220/36* (2013.01); *C08F 226/02* (2013.01); *C08F 230/02* (2013.01); *C08F 265/06* (2013.01); *C08J 3/28* (2013.01); *C08J 7/047* (2013.01); *C09D 4/06* (2013.01); *C09D 5/24* (2013.01); *C09D 153/00* (2013.01); *C08F 2220/285* (2013.01); *C08F 2220/346* (2013.01); *C08F 2222/225* (2013.01); *C08J 2335/02* (2013.01); *C08J 2367/02* (2013.01); *C08J 2453/00* (2013.01); *C08K 5/07* (2013.01); *C09D 5/32* (2013.01)

(58) Field of Classification Search
CPC .......... C08F 2/005; C08F 2/48; C08F 220/28; C08F 220/34; C08F 220/36; C08F 226/02; C08F 230/02; C08F 265/06; C08F 293/00; C08F 2220/285; C08F 2220/346; C08F 2222/225; C08J 3/28; C08J 7/047; C08J 2367/02; C08J 2453/00; C08J 2335/02; C09D 4/06; C09D 5/24; C09D 5/32; C09D 153/00; C07C 45/63; C07C 67/08; C07C 67/293; C08K 5/07; B05D 3/06
See application file for complete search history.

(56) References Cited

U.S. PATENT DOCUMENTS

| | | | | |
|---|---|---|---|---|
| 8,216,353 B2* | 7/2012 | Nakamura | ........... | C09D 11/101 |
| | | | | 106/31.13 |
| 9,914,788 B2* | 3/2018 | Yamashita | ................ | C08F 2/44 |

(Continued)

FOREIGN PATENT DOCUMENTS

| | | | |
|---|---|---|---|
| JP | 2008-247939 A | 10/2008 | |
| JP | 2011-012240 A | 1/2011 | |

(Continued)

OTHER PUBLICATIONS

Communication dated Mar. 27, 2018 from the Japanese Patent Office in counterpart Japanese application No. 2016-551887.

(Continued)

*Primary Examiner* — Sanza L. McClendon
(74) *Attorney, Agent, or Firm* — Sughrue Mion, PLLC

(57) ABSTRACT

Provided are an active energy ray-curable composition that has good antistatic properties, scratch resistance, and transparency after curing, and an antistatic film using the same. The active energy ray-curable composition of the present invention is an active energy ray-curable composition, including a photopolymerization initiator A represented by the following Formula (I), an antistatic polymer B, and a polymerizable compound C containing an ethylenically unsaturated group,

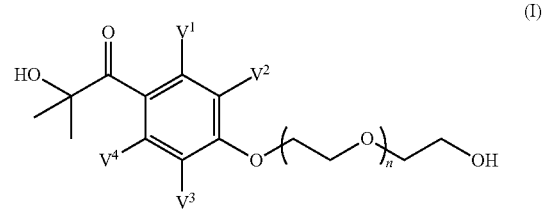

in Formula (I), $V^1$, $V^2$, $V^3$, and $V^4$ each independently represent a hydrogen atom or a substituent, and n represents an integer of 1 to 5.

18 Claims, No Drawings

(51) Int. Cl.
  *C08F 230/02* (2006.01)
  *C08J 3/28* (2006.01)
  *C09D 5/24* (2006.01)
  *C09D 153/00* (2006.01)
  *C09D 5/32* (2006.01)
  *C08F 222/22* (2006.01)
  *C08K 5/07* (2006.01)

(56) References Cited

U.S. PATENT DOCUMENTS

2008/0241424 A1 10/2008 Nakamura
2015/0353748 A1* 12/2015 Yofu .................... C09D 11/101
                                                  347/21

FOREIGN PATENT DOCUMENTS

JP   2011-225797 A   11/2011
WO   2014/148290 A1   9/2014

OTHER PUBLICATIONS

Communication dated Nov. 24, 2017, issued by the Korean Intellectual Property Office in corresponding Korean Application No. 10-2017-7007104.
International Search Report for PCT/JP2015/075826 dated Dec. 8, 2015 [PCT/ISA/210].
Written Opinion for PCT/JP2015/075826 dated Dec. 8, 2015 [PCT/ISA/237].
International Preliminary Report on Patentability with translation of Written Opinion dated Apr. 13, 2017, issued by the International Searching Authority in application No. PCT/JP2015/075826.
Communication dated Jan. 29, 2018, from State Intellectual Property Office of the P.R.C. in counterpart application No. 201580051384.2.
The Second Office Action, dated Sep. 29, 2018, in corresponding Chinese Application No. 201580051384.2, 15 pages in English and Chinese.
Communication dated Apr. 3, 2019, from the State intellectual Property Office of the P.R.C.in counterpart application No. 201580051384.2.

* cited by examiner

ACTIVE ENERGY RAY-CURABLE COMPOSITION AND ANTISTATIC FILM

CROSS-REFERENCE TO RELATED APPLICATIONS

This application is a Continuation of PCT International Application No. PCT/JP2015/075826 filed on Sep. 11, 2015, which claims priority under 35 U.S.C. § 119(a) to Japanese Patent Application No. 2014-199083 filed on Sep. 29, 2014. The above application is hereby expressly incorporated by reference, in its entirety, into the present application.

BACKGROUND OF THE INVENTION

1. Field of the Invention

The present invention relates to an active energy ray-curable composition and an antistatic film.

2. Description of the Related Art

Generally, resin materials exhibit excellent electrical insulation properties and are therefore very useful for applications requiring electrical insulating properties such as insulators, but surfaces thereof are easily charged with static electricity, which is thus likely to result in dust adsorption and electrostatic troubles.

To solve such problems, it is known to use various antistatic agents (in particular, cationic antistatic agents).

For example, JP2011-225797A discloses an "antistatic coating composition including an antistatic copolymer (A) having a quaternary ammonium base in the molecule, a compound (B) having three or more ethylenically unsaturated groups, a photopolymerization initiator (C) containing a photopolymerization initiator (c-1) having a solubility in water of 0.2 g/L or less and a photopolymerization initiator (c-2) having a solubility in water of 1 g/L or more, and a solvent (D) containing an alcohol-based solvent (d-1)" ([claim 1]), and also discloses that the photopolymerization initiator (C) is "at least one selected from the group consisting of 1-hydroxy-cyclohexyl-phenyl-ketone, 2-methyl-1-[4-(methylthio)phenyl]-2-morpholinopropan-1-one, bis(2,4,6-trimethylbenzoyl)-phenylphosphine oxide, 2-hydroxy-1-{4-[4-(2-hydroxy-2-methyl-propionyl)-benzyl]-phenyl}-2-methyl-propan-1-one, 2,4,6-trimethylbenzoyl-diphenyl-phosphine oxide, oligo {2-hydroxy-2-methyl-1-[4-(1-methylvinyl)phenyl]propanone}, and 2,4,6-trimethylbenzophenone" ([claim 4]).

SUMMARY OF THE INVENTION

The present inventors have studied the antistatic coating composition described in JP2011-225797A and have found that, depending on the type and combination of copolymers and photopolymerization initiators to be used, there is a case where antistatic properties may be poor and there is also a case where scratch resistance and transparency may be inferior.

Accordingly, an object of the present invention is to provide an active energy ray-curable composition that has good antistatic properties, scratch resistance, and transparency after curing, and an antistatic film using the same.

As a result of extensive studies to achieve the above-mentioned object, the present inventors have found that a composition containing a polymer having antistatic properties and a polymerizable compound, together with a photopolymerization initiator having a specific structure, becomes good in all of antistatic properties, scratch resistance, and transparency after curing. The present invention has been completed based on such a finding.

That is, it has been found that it is possible to achieve the foregoing object by the following configurations.

[1] An active energy ray-curable composition, comprising: a photopolymerization initiator A represented by Formula (I) to be described hereinafter; an antistatic polymer B; and a polymerizable compound C containing an ethylenically unsaturated group.

[2] The active energy ray-curable composition according to [1], in which the antistatic polymer B is a polymer having at least one repeating unit selected from the group consisting of repeating units represented by Formulae (1) to (5) to be described hereinafter.

[3] The active energy ray-curable composition according to [2], in which the antistatic polymer B is a cationic polymer having a repeating unit represented by Formula (1) to be described hereinafter.

[4] The active energy ray-curable composition according to [2] or [3], in which the repeating unit represented by Formula (1) to be described hereinafter is an ammonium salt represented by Formula (6) to be described hereinafter.

[5] The active energy ray-curable composition according to any one of [2] to [4], in which the antistatic polymer B contains at least one repeating unit selected from the group consisting of repeating units represented by Formulae (1) to (5) to be described hereinafter and a repeating unit represented by Formula (7) to be described hereinafter.

[6] The active energy ray-curable composition according to any one of [2] to [5], in which the antistatic polymer B contains a repeating unit represented by Formula (1) to be described hereinafter and a repeating unit represented by Formula (3) or (4) to be described hereinafter.

[7] The active energy ray-curable composition according to [6], in which the repeating unit represented by Formula (3) to be described hereinafter is a repeating unit represented by Formula (8) to be described hereinafter.

[8] The active energy ray-curable composition according to any one of [2] to [7], in which the antistatic polymer B contains at least one repeating unit selected from the group consisting of repeating units represented by Formulae (1) to (5) to be described hereinafter and a repeating unit derived from a monomer having a CLogP value of 0.3 to 5.

[9] The active energy ray-curable composition according to any one of [2] to [8], in which the antistatic polymer B is a copolymer containing 40 to 80 mass % of repeating units represented by Formulae (1) to (5) to be described hereinafter.

[10] The active energy ray-curable composition according to [9], in which the antistatic polymer B contains 40 to 80 mass % of repeating units represented by Formulae (1) to (5) to be described hereinafter, and 20 to 60 mass % of a repeating unit represented by Formula (7) to be described hereinafter.

[11] The active energy ray-curable composition according to [9] or [10], in which the antistatic polymer B contains 39.5 to 70 mass % of a repeating unit represented by Formula (1) to be described hereinafter, 20 to 60 mass % of a repeating unit represented by Formula (7) to be described hereinafter, and 0.5 to 10 mass % of a repeating unit represented by Formula (3) or (4) to be described hereinafter.

[12] The active energy ray-curable composition according to any one of [1] to [11], in which the polymerizable compound C is a methacrylic or acrylic compound.

[13] The active energy ray-curable composition according to any one of [1] to [12], in which the molecular weight of the polymerizable compound C is 90 to 5,000.

[14] The active energy ray-curable composition according to any one of [1] to [13], in which the content of the photopolymerization initiator A is 0.5 to 10 parts by mass with respect to 100 parts by mass of the polymerizable compound C.

[15] The active energy ray-curable composition according to any one of [1] to [14], in which the content of the polymer B is 1 to 40 parts by mass with respect to 100 parts by mass of the polymerizable compound C.

[16] The active energy ray-curable composition according to any one of [1] to [15], in which the photopolymerization initiator A has n of 1 in Formula (I) to be described hereinafter.

[17] The active energy ray-curable composition according to any one of [1] to [16], which is used in an antistatic agent.

[18] An antistatic film comprising an antistatic layer formed by applying the active energy ray-curable composition according to any one of [1] to [17] onto a substrate and curing the applied composition by active energy rays.

According to the present invention, it is possible to provide an active energy ray-curable composition that has good antistatic properties, scratch resistance, and transparency after curing, and an antistatic film using the same.

DESCRIPTION OF THE PREFERRED EMBODIMENTS

Hereinafter, the present invention will be described in detail.

The description of constituent features given below is often made based on representative embodiments of the present invention, but the present invention is not limited to such embodiments.

Further, the numerical value ranges shown with "to" in the present specification means ranges including the numerical values indicated before and after "to" as the lower limit and the upper limit, respectively.

[Active Energy Ray-Curable Composition]

The active energy ray-curable composition of the present invention (hereinafter, also referred to as the "composition of the present invention") is an active energy ray-curable composition containing a photopolymerization initiator A represented by Formula (I) to be described hereinafter, an antistatic polymer B, and a polymerizable compound C containing an ethylenically unsaturated group.

By including a photopolymerization initiator A, an antistatic polymer B, and a polymerizable compound C, the composition of the present invention becomes good in all of antistatic properties, scratch resistance, and transparency after curing.

The reason why all of antistatic properties, scratch resistance, and transparency become good is not clear in detail, but it is approximately thought that the following is true.

First, it is believed that compatibility of the photopolymerization initiator A and the antistatic polymer B is increased due to the presence of the ethylene oxide structure (hereinafter, also referred to as "EO chain") represented by the predetermined number n of repeating units, in the structure of the photopolymerization initiator A represented by the following Formula (I).

Further, it is believed that the antistatic polymer B also exhibits high compatibility with the polymerizable compound C, in other words, the polymerizable compound C functions as a solvent for the antistatic polymer B.

Therefore, it is considered that in the system containing the photopolymerization initiator A, the antistatic polymer B, and the polymerizable compound C, the photopolymerization initiator A is uniformly dispersed in the polymerizable compound C due to the presence of the antistatic polymer B.

Then, it can be considered that, after an active species is generated by active energy rays, a portion of EO chains derived from the photopolymerization initiator A is linked to the terminal of the polymer of the polymerizable compound C, leading to expression of a surface activating ability, and consequently, the antistatic polymer B and the polymer of the polymerizable compound C can be localized on the surface, whereby antistatic properties and scratch resistance become good.

Further, it is considered that, as a result of increased compatibility of the photopolymerization initiator A and the antistatic polymer B, it is possible to not only localize the antistatic polymer B or the polymer of the polymerizable compound C on the surface, but also to uniformly disperse the antistatic polymer B or the polymer of the polymerizable compound C in the cured product, so transparency becomes good.

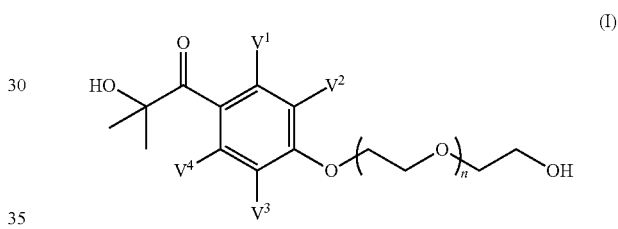

(I)

Further, it was found that, by incorporation of the photopolymerization initiator A, the antistatic polymer B, and the polymerizable compound C, surprisingly, the composition of the present invention also becomes good in antistatic properties under a low humidity environment, and a change (deterioration) in the antistatic properties was not observed even after a thermocycle test.

This can be considered that antistatic properties become good even under a low humidity environment, because the residue containing the above-mentioned EO chains derived from the photopolymerization initiator A not only has a surface activating ability, but also contributes to moisture-retaining properties.

Further, it is considered that, as described above, the compatibility of the photopolymerization initiator A and the polymer B is increased and, as a result, the photopolymerization initiator A can be uniformly dispersed in the cured product, consequently aggregation of the unreacted polymerizable compound can be suppressed, whereby deterioration in the antistatic properties was not observed even after a thermocycle test.

Hereinafter, the photopolymerization initiator A, the antistatic polymer B, and the polymerizable compound C contained in the composition of the present invention will be described in detail.

[Photopolymerization Initiator A]

The photopolymerization initiator A contained in the composition of the present invention is a photopolymerization initiator represented by the following Formula (I).

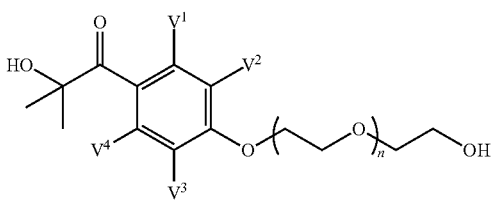

(I)

In Formula (I), $V^1$, $V^2$, $V^3$, and $V^4$ each independently represent a hydrogen atom or a substituent, and n represents an integer of 1 to 5.

In the present invention, when n in Formula (I) is an integer of 1 to 5, the function by the action of the above-mentioned EO chain is expressed, and therefore antistatic properties, scratch resistance, and transparency after curing become good.

In terms of that these effects are further improved, n in Formula (I) is preferably an integer of 1 to 3, more preferably an integer of 1 or 2, and still more preferably 1.

In $V^1$ to $V^4$, examples of the substituent include a halogen atom, an alkyl group, an alkoxy group, a hydroxy group, an alkylthio group, a mercapto group, an acyl group, and an amino group.

In $V^1$ to $V^4$, the halogen atom is preferably a fluorine atom, a chlorine atom, a bromine atom, or an iodine atom, more preferably a chlorine atom or a bromine atom, and particularly preferably a chlorine atom.

In $V^1$ to $V^4$, the number of carbon atoms in the alkyl group is preferably 1 to 6 and more preferably 1 to 3.

In $V^1$ to $V^4$, the alkyl group may be a linear alkyl group or a branched alkyl group. Further, the alkyl group may have an alicyclic structure.

Examples of the alkyl group in $V^1$ to $V^4$ include a methyl group, an ethyl group, an n-propyl group, an isopropyl group, an n-butyl group, a sec-butyl group, a tert-butyl group, an n-pentyl group, an n-hexyl group, and a cyclohexyl group. Preferred is a methyl group, an ethyl group, an n-propyl group, or an isopropyl group.

In $V^1$ to $V^4$, the number of carbon atoms in the alkoxy group is preferably 1 to 6 and more preferably 1 to 3.

In $V^1$ to $V^4$, the alkoxy group may be a linear alkoxy group or a branched alkoxy group. Further, the alkoxy group may have an alicyclic structure.

Examples of the alkoxy group in $V^1$ to $V^4$ include a methoxy group, an ethoxy group, an n-propyloxy group, an isopropyloxy group, an n-butoxy group, a sec-butoxy group, a tert-butoxy group, an n-pentyloxy group, an n-hexyloxy group, and a cyclohexyloxy group. Preferred is a methoxy group, an ethoxy group, an n-propyloxy group, or an isopropyloxy group.

In $V^1$ to $V^4$, the number of carbon atoms in the alkylthio group is preferably 1 to 6 and more preferably 1 to 4.

In $V^1$ to $V^4$, the alkylthio group may be a linear alkylthio group or a branched alkylthio group. Further, an alkylthio group may have an alicyclic structure.

Examples of the alkylthio group in $V^1$ to $V^4$ include a methylthio group, an ethylthio group, an n-propylthio group, an isopropylthio group, an n-butylthio group, a sec-butylthio group, a tert-butylthio group, an n-pentylthio group, an n-hexylthio group, and a cyclohexylthio group. Preferred is a methylthio group, an ethylthio group, an n-propylthio group, or an isopropylthio group.

In $V^1$ to $V^4$, the number of carbon atoms in the acyl group is preferably 1 to 6 and more preferably 1 to 3.

In $V^1$ to $V^4$, the acyl group may be a linear acyl group or a branched acyl group.

Examples of the acyl group in $V^1$ to $V^4$ include a formyl group, an acetyl group, an ethylacyl group, an n-propylacyl group, and an isopropylacyl group. Preferred is a formyl group, an acetyl group, or an ethylacyl group.

$V^1$ to $V^4$ are preferably a hydrogen atom, a halogen atom, an alkyl group, an alkoxy group, or an alkylthio group, more preferably a hydrogen atom, an alkoxy group, or an alkylthio group, and most preferably a hydrogen atom.

Further, a more preferred form of the compound represented by Formula (I) may be, for example, a form in which two or more (preferably three or more, and most preferably four) of $V^1$ to $V^4$ are a hydrogen atom.

Specific examples of the compound represented by Formula (I) (exemplary compounds) are shown below, but the compound represented by Formula (I) is not limited thereto.

TABLE 1

(I)

| Exemplary compounds | n | $V^1$ | $V^2$ | $V^3$ | $V^4$ |
| --- | --- | --- | --- | --- | --- |
| (I)-1 | 1 | H | H | H | H |
| (I)-2 | 2 | H | H | H | H |
| (I)-3 | 3 | H | H | H | H |
| (I)-4 | 5 | H | H | H | H |
| (I)-5 | 1 | $CH_3$ | H | H | H |
| (I)-6 | 1 | H | $CH_3$ | H | H |
| (I)-7 | 1 | H | $OCH_3$ | H | H |
| (I)-8 | 1 | H | Cl | H | H |
| (I)-9 | 1 | H | Br | H | H |
| (I)-10 | 1 | H | OH | H | H |
| (I)-11 | 1 | Cl | Cl | H | H |
| (I)-12 | 1 | $SCH_3$ | H | H | H |
| (I)-13 | 2 | Cl | H | Cl | H |
| (I)-14 | 2 | H | $CH_3$ | H | H |
| (I)-15 | 2 | H | $N(CH_3)_2$ | Cl | H |
| (I)-16 | 2 | $CH_3$ | $CH_3$ | H | H |
| (I)-17 | 3 | H | OH | H | H |
| (I)-18 | 3 | H | $CH_3$ | H | H |
| (I)-19 | 5 | H | $COCH_3$ | H | H |
| (I)-20 | 5 | H | $CH_3$ | H | H |

The compound (polymerization initiator) represented by Formula (I) can be synthesized in accordance with the method described, for example, in paragraphs [0067] to [0071] and [0112] to [0115] of JP2000-186242A.

In the present invention, the content of the photopolymerization initiator A is preferably 0.5 to 10 parts by mass and more preferably 1 to 8 parts by mass with respect to 100 parts by mass of a polymerizable compound C to be described hereinafter, from the viewpoint of curability, moisture-retaining properties under a low humidity environment, and dispersibility of the unreacted polymerizable compound C.

Further, in the present invention, other initiators may be used in combination in addition to the above-mentioned photopolymerization initiator A.

Examples of other initiators include photo-radical polymerization initiators. Specifically, a hydroxyacetophenone compound, an aminoacetophenone compound, and an acylphosphine compound can also be suitably used.

More specifically, for example, aminoacetophenone-based initiators described in JP1998-291969A (JP-H10-291969A), and acylphosphine oxide-based initiators described in JP4225898B may also be used.

Commercially available products IRGACURE-184, DAROCUR-1173, IRGACURE-500, IRGACURE-2959 and IRGACURE-127 (trade names, all manufactured by BASF Corporation) may be used as the hydroxyacetophenone-based initiator. Commercially available products IRGACURE-907, IRGACURE-369 and IRGACURE-379 (trade names, all manufactured by BASF Corporation) may be used as the aminoacetophenone-based initiator. The compounds described in JP2009-191179A, whose absorption wavelength is matched to a light source having a long wavelength such as 365 nm or 405 nm, may also be used as the aminoacetophenone-based initiator. Commercially available products IRGACURE-819 and DAROCUR-TPO (trade names, both manufactured by BASF Corporation) may be used as the acylphosphine-based initiator.

[Antistatic Polymer B]

The antistatic polymer B contained in the composition of the present invention is not particularly limited and may be a conventionally known polymer having antistatic properties.

In the present invention, in terms of that antistatic properties after curing become better and reactivity with the photopolymerization initiator A becomes good, the antistatic polymer B is preferably a polymer having at least one repeating unit selected from the group consisting of repeating units represented by the following Formulae (1) to (5).

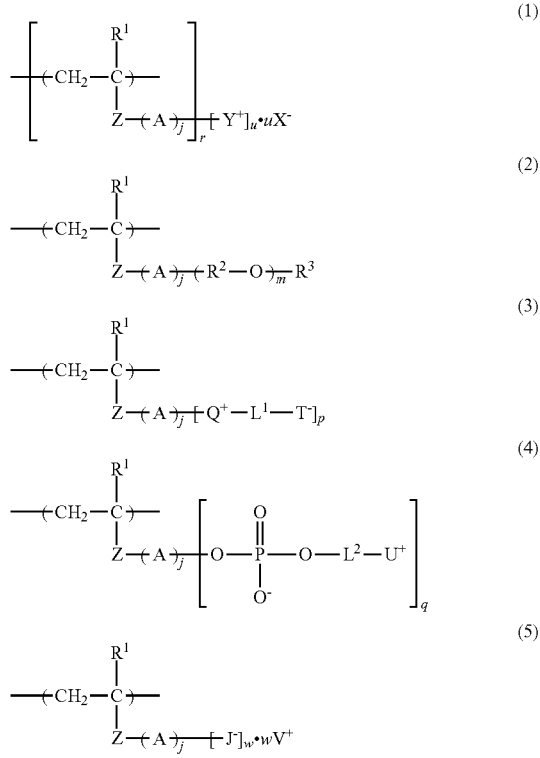

In Formulae (1) to (5), $R^1$'s each independently represent a hydrogen atom, a halogen atom, a cyano group, a monovalent hydrocarbon group, —COO—$C_2$, or —COO—$C_2$ bonded through a hydrocarbon, and $C_2$ represents a hydrogen atom or a hydrocarbon group which may have a substituent.

In Formulae (1) to (5), Z's each independently represent —COO—, —CONH—, —OCO—, —CH$_2$OCO—, —CH$_2$COO—, —O—, —SO$_2$—, —CO—, —CONHCOO—, —CONHCONH—, —CONHSO$_2$—, —CON(P$_3$)—, —SO$_2$N(G)-, —C$_6$H$_4$—, or an alkylene group having 1 to 30 carbon atoms, and G represents a hydrogen atom or a hydrocarbon group.

In Formulae (1) to (5), A's each independently represent a single bond or a divalent or higher valent linking group, and j's each independently represent an integer of 0 to 30.

In Formula (1), $Y^+$ represents a cationic group, $X^-$ represents an anionic group, u represents an integer of 1 to 3, and r represents an integer of 1 to 4.

In Formula (2), $R^2$ represents an alkylene group having 2 to 5 carbon atoms which may have a substituent, $R^3$ represents a hydrogen atom or an alkyl group having 1 to 5 carbon atoms which may have a substituent, and m represents an integer of 2 to 200.

In Formula (3), represents an ammonium cation, a sulfonium cation, an iodonium cation, a phosphonium cation, or a pyridinium cation, $L^1$ represents a single bond or a divalent or higher valent linking group, $T^-$ represents COO$^-$, SO$_3^-$ or OPO(O$^-$)(ORp), and Rp represents an alkyl group. p represents an integer of 1 to 3.

In Formula (4), $L^2$ represents a single bond or a divalent or higher valent linking group, $U^+$ represents an ammonium or phosphonium cation which may have a substituent, and q represents an integer of 1 to 3.

In Formula (5), $J^-$ represents COO$^-$, OPO(OH)O$^-$ or SO$_3^-$, $V^+$ represents a cationic group, and w represents an integer of 1 to 3.

Here, $R^1$ in Formulae (1) to (5) is preferably a hydrogen atom or a monovalent hydrocarbon group. Examples of the monovalent hydrocarbon group include alkyl groups having 1 to 10 carbon atoms. Among them, preferred is a methyl group.

Z in Formulae (1) to (5) is preferably —COO—, —CONH—, or an alkylene group having 1 to 30 carbon atoms. Examples of the alkylene group having 1 to 30 carbon atoms include a methylene group, an ethylene group, and a propylene group. Among them, preferred is a methylene group.

A in Formulae (1) to (5) is preferably a single bond or a divalent linking group. Examples of the divalent linking group include alkylene groups having 1 to 10 carbon atoms. Among them, preferred is an ethylene group or a propylene group.

$Y^+$ (cationic group) in Formula (1) is preferably an ammonium cation. Examples of $X^-$ (anionic group) include Cl$^-$, Br$^-$, I$^-$, SO$_3^-$, NCS$^-$, ROSO$_3^-$, ROSO$_2^-$, RSO$_3^-$, R—C$_6$H$_4$—SO$_3^-$, (RO)$_2$PO$_2^-$, R$_4$B$^-$ (in which R represents an alkyl group which may have a substituent, an alicyclic alkyl group, or an aromatic group), (CF$_3$SO$_2$)$_2$N$^-$, and (SO$_2$C$_2$F$_5$)$_2$N$^-$.

$R^2$ in Formula (2) is preferably an ethylene group, $R^3$ is preferably a hydrogen atom or an alkyl group having 1 to 3 carbon atoms, and m is preferably an integer of 2 to 30.

$Q^+$ in Formula (3) is preferably an ammonium cation. $L^1$ is preferably a single bond or a divalent linking group. Examples of the divalent linking group include alkylene groups having 1 to 10 carbon atoms. Among them, preferred is a methylene group, an ethylene group, a propylene group or a butylene group. $T^-$ is preferably COO$^-$ or SO$_3^-$.

$L^2$ in Formula (4) is preferably a single bond or a divalent linking group. Examples of the divalent linking group include alkylene groups having 1 to 10 carbon atoms.

Among them, preferred is a methylene group, an ethylene group, a propylene group or a butylene group. $U^+$ is preferably an ammonium cation.

$J^-$ in Formula (5) is preferably $SO_3^-$. Examples of the cationic group of $V^+$ include $Na^+$, $K^+$, a quaternary ammonium cation, and a pyridinium cation.

In the present invention, in terms of that antistatic properties after curing become better and compatibility with the photopolymerization initiator A becomes better, the antistatic polymer B is preferably a cationic polymer having a repeating unit represented by Formula (1) among polymers having repeating units represented by Formulae (1) to (5), and the repeating unit represented by Formula (1) is preferably an ammonium salt represented by the following Formula (6).

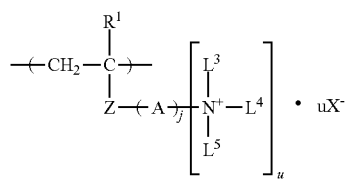

(6)

In Formula (6), $R^1$ and A each have the same definition of $R^1$ and A in Formula (1).

Z represents —COO—, —CONH—, or —CH$_2$—, and j represents an integer of 0 to 10.

$L^3$, $L^4$, and $L^5$ each independently represent an alkyl group, alkenyl group, alkynyl group, aryl group or heterocyclic group having 1 to 20 carbon atoms which may have a substituent, and at least two of $L^3$, $L^4$, and $L^5$ may be bonded to each other to form a ring.

Specific examples of monomers capable of generating polymers having repeating units represented by Formulae (1) and (6) include (B)-a1-1 to (B)-a1-11 shown below.

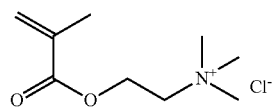
(B)-a1-1

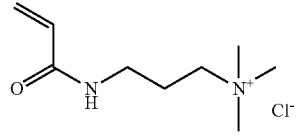
(B)-a1-2

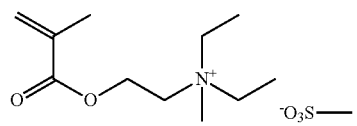
(B)-a1-3

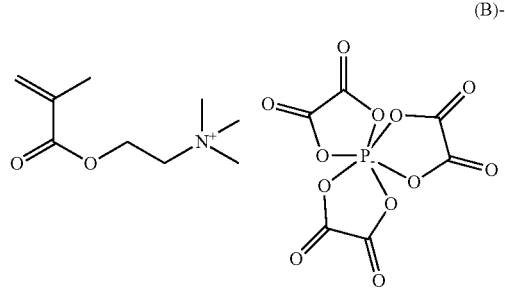
(B)-a1-4

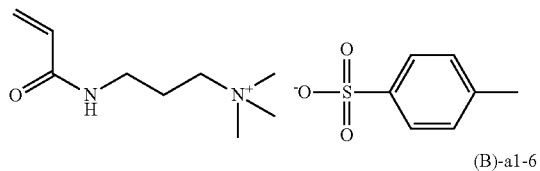
(B)-a1-5

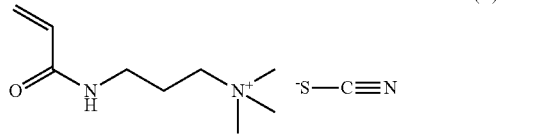
(B)-a1-6

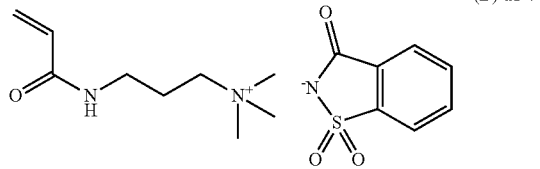
(B)-a1-7

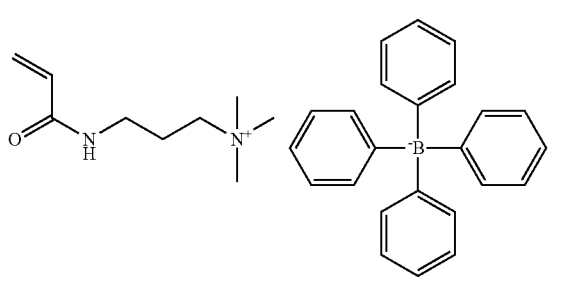
(B)-a1-8

(B)-a1-9

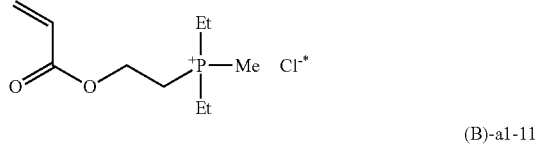
(B)-a1-10

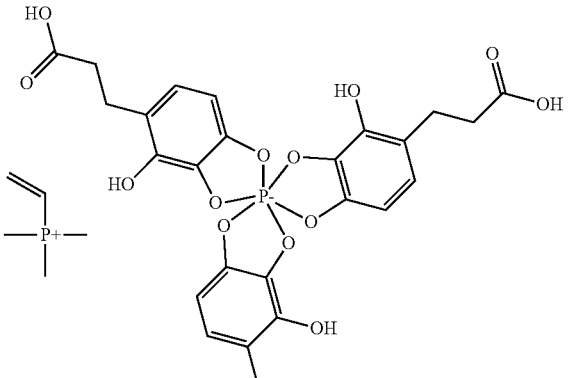
(B)-a1-11

Specific examples of monomers capable of generating a polymer having a repeating unit represented by Formula (2) include (B)-a2-1 to (B)-a2-3 shown below.

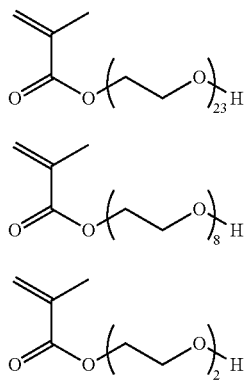

Specific examples of monomers capable of generating a polymer having a repeating unit represented by Formula (3) include (B)-a3-1 to (B)-a3-7 shown below.

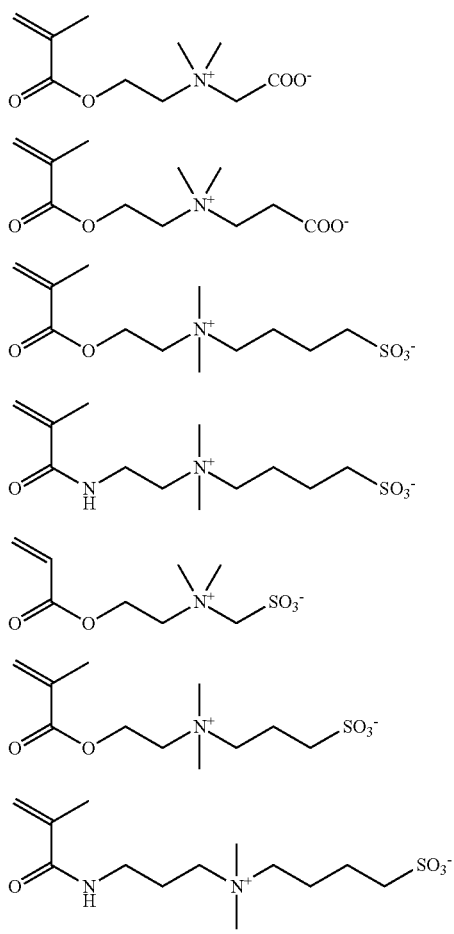

Specific examples of monomers capable of generating a polymer having a repeating unit represented by Formula (4) include (B)-a4-1 to (B)-a4-2 shown below.

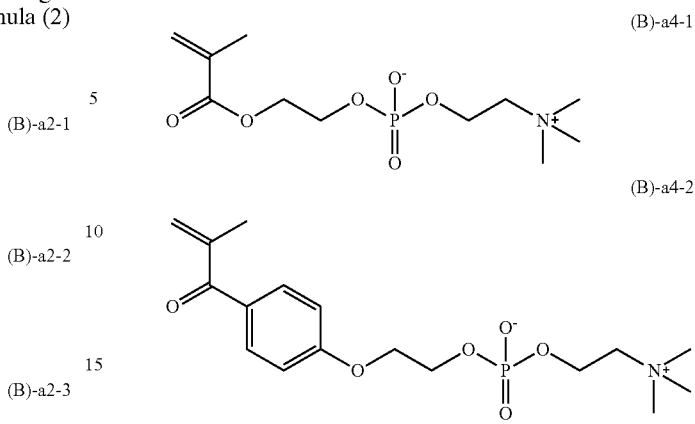

Specific examples of monomers capable of generating a polymer having a repeating unit represented by Formula (5) include (B)-a5-1 shown below.

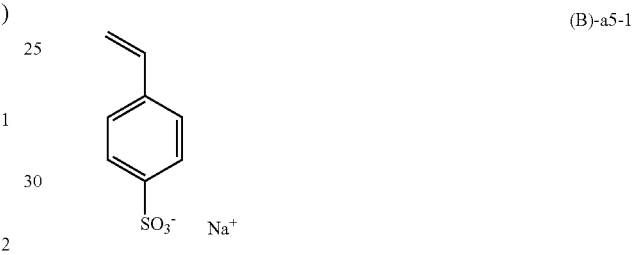

<Copolymer B1>

In the present invention, the antistatic polymer B is preferably a copolymer containing at least one repeating unit selected from the group consisting of repeating units represented by Formulae (1) to (5) and a repeating unit represented by Formula (7) (hereinafter, also referred to as "copolymer B1"), in terms of that compatibility with the photopolymerization initiator A becomes good.

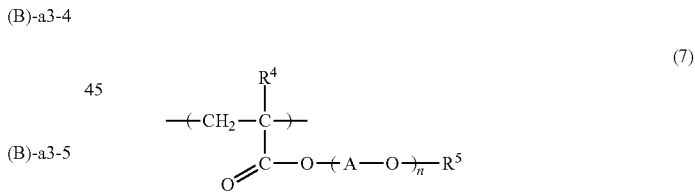

In Formula (7), $R^4$ represents a hydrogen atom or $CH_3$, $R^5$ represents a hydrogen atom or a hydrocarbon group having 6 to 25 carbon atoms which may have a substituent, A represents an alkylene group having 2 to 5 carbon atoms which may have a substituent, and n represents an integer of 3 to 50.

Specific examples of monomers capable of generating a repeating unit represented by Formula (7) include (B)-b-1 to (B)-b-5 shown below.

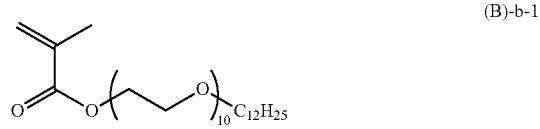

(B)-b-2
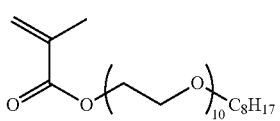

(B)-b-3
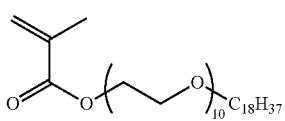

(B)-b-4
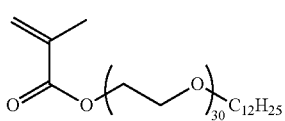

(B)-b-5
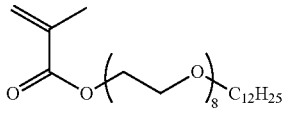

<Copolymer B2>

In the present invention, the antistatic polymer B is preferably a copolymer containing the repeating unit represented by Formula (1) and the repeating unit represented by Formula (3) or (4) (hereinafter, also referred to as "copolymer B2"), in terms of that compatibility with the photopolymerization initiator A is high and antistatic properties become better, thus the antistatic properties being less likely to deteriorate even after a thermocycle test.

In a case where the antistatic polymer B is a copolymer B2, the repeating unit represented by Formula (3) is preferably a repeating unit represented by Formula (8) in terms of that antistatic properties after curing become better and compatibility with the photopolymerization initiator A becomes good.

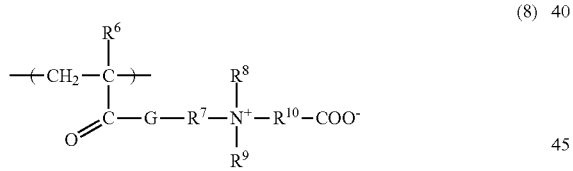
(8)

In Formula (8), $R^6$ represents a hydrogen atom or $CH_3$, $R^7$ represents an alkylene group having 1 to 6 carbon atoms, $R^8$ and $R^9$ each independently represent an alkyl group having 1 to 4 carbon atoms, and $R^{10}$ represents an alkylene group having 1 to 4 carbon atoms.

<Copolymer B3>

In the present invention, the antistatic polymer B is preferably a copolymer containing at least one repeating unit selected from the group consisting of repeating units represented by Formulae (1) to (5) and a repeating unit derived from a monomer having a CLogP value of 0.3 to 5 (hereinafter, also referred to as "copolymer B3"), in terms of that compatibility with the photopolymerization initiator A becomes good.

As used herein, the term "CLogP value" refers to a value determined by calculating common logarithm log P of the partition coefficient P in 1-octanol and water. The calculation of ClogP values employed the system of Daylight Chemical Information Systems, Inc.: CLOGP program embedded in PCModels.

Examples of the monomer having a CLogP value of 0.3 to 5 include a (meth)acrylic monomer and a (meth)acrylamide monomer. Specific examples thereof include (B)-d-1 to (B)-d-10 shown below.

As used herein, the term "(meth)acrylic" is notation of a concept that includes methacrylic or acrylic.

B-d-1
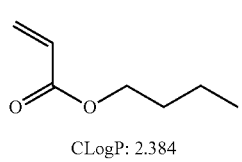
CLogP: 2.384

B-d-2
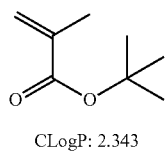
CLogP: 2.343

B-d-3
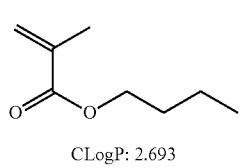
CLogP: 2.693

B-d-4
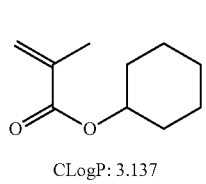
CLogP: 3.137

B-d-5
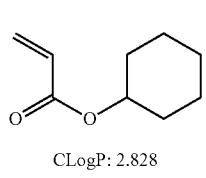
CLogP: 2.828

B-d-6
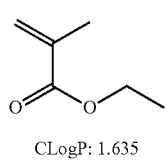
CLogP: 1.635

B-d-7
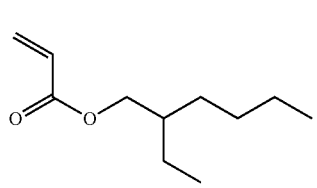
CLogP: 4.37

B-d-8
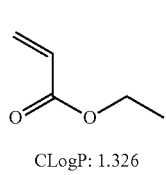
CLogP: 1.326

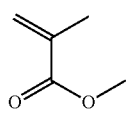

CLogP: 1.106

B-d-9

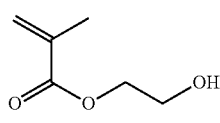

CLogP: 0.3032

B-d-10

In the present invention, in a case where the antistatic polymer B is the above-mentioned copolymers B1 to B3, in terms of that compatibility with the photopolymerization initiator A is high and antistatic properties become better, the antistatic polymer B is preferably a copolymer containing 40 to 80 mass % of repeating units represented by Formulae (1) to (5).

Specifically, the antistatic polymer B is preferably a copolymer containing 40 to 80 mass % of repeating units represented by Formulae (1) to (5) and 20 to 60 mass % of a repeating unit represented by Formula (7) and more preferably a copolymer containing 45 to 75 mass % of repeating units represented by Formulae (1) to (5) and 25 to 55 mass % of a repeating unit represented by Formula (7).

In particular, the antistatic polymer B is preferably a copolymer containing 39.5 to 70 mass % of a repeating unit represented by Formula (1), 20 to 60 mass % of a repeating unit represented by Formula (7), and 0.5 to 10 mass % of a repeating unit represented by Formula (3) or (4).

In the present invention, the method for preparing the antistatic polymer B is not particularly limited, and the antistatic polymer B can be prepared by polymerizing the above-mentioned polymerizable compound using a conventionally known polymerization initiator (in particular, a radical initiator).

Specific examples of the radical initiator include organic peroxides such as benzoyl peroxide, halogen benzoyl peroxide, lauroyl peroxide, acetyl peroxide, dibutyl peroxide, cumene hydroperoxide, and butyl hydroperoxide; inorganic peroxides such as hydrogen peroxide, ammonium persulfate, and potassium persulfate; azo compounds such as 2,2'-azobis(isobutyronitrile), 2,2'-azobis(propionitrile), and 1,1'-azobis(cyclohexanecarbonitrile); and diazo compounds such as diazoaminobenzene and p-nitrobenzene diazonium.

In the present invention, the weight-average molecular weight of the antistatic polymer B is preferably greater than 5,000 and more preferably 7,000 to 500,000.

The weight-average molecular weight is measured by a gel permeation chromatography (GPC) method and can be determined in terms of standard polystyrene.

In the present invention, the content of the antistatic polymer B is preferably 1 to 40 parts by mass and more preferably 5 to 30 parts by mass with respect to 100 parts by mass of a polymerizable compound C to be described hereinafter, in terms of that antistatic properties and scratch resistance after curing become better.

[Polymerizable Compound C]

The polymerizable compound C having an ethylenically unsaturated group contained in the composition of the present invention is not particularly limited.

Specific examples of the ethylenically unsaturated group include polymerizable functional groups such as a (meth) acryloyl group, a vinyl group, a styryl group, and an allyl group.

In the present invention, the molecular weight of the polymerizable compound C is preferably 90 to 5,000 and more preferably 100 to 4,000, in terms of that antistatic properties and scratch resistance after curing become better.

Further, in the present invention, the polymerizable compound C is preferably a methacrylic or acrylic compound (hereinafter, also referred to as "(meth)acrylic compound") containing a methacryloyl group or acryloyl group as the ethylenically unsaturated group, in terms of that compatibility with the photopolymerization initiator A becomes higher.

Examples of the (meth)acrylic compound include polyfunctional (meth)acrylate, polyfunctional (meth)acrylamide, monofunctional (meth)acrylate, and monofunctional (meth) acrylamide. These compounds may be used alone or in combination of two or more thereof.

<Polyfunctional (Meth)Acrylate and Polyfunctional (Meth)Acrylamide>

Specific examples of the polyfunctional (meth)acrylate include trimethylolpropane tri(meth)acrylate, pentaerythritol tri(meth)acrylate, pentaerythritol tetra (meth)acrylate, dipentaerythritol penta(meth)acrylate, dipentaerythritol hexa(meth)acrylate [hereinafter, dipentaerythritol hexaacrylate is also referred to simply as "DPHA"], dipentaerythritol penta(meth)acrylate, dipentaerythritol tetra(meth)acrylate, neopentyl glycol di(meth)acrylate, diethylene glycol di(meth)acrylate, trimethylolethane tri(meth)acrylate, trimethylolpropane tri(meth)acrylate, 1,6-hexanediol di(meth)acrylate, tripropylene glycol di(meth)acrylate, tricyclodecane dimethanol di(meth)acrylate, and tetraethylene glycol di(meth) acrylate. These compounds may be used alone or in combination of two or more thereof.

Specific examples of the polyfunctional (meth)acrylamide include N,N'-methylenebis(meth)acrylamide, 1,2-bis[(meth) acrylamide]ethane, 1,3-bis[(meth)acrylamide]propane, 1,6-bis[(meth)acrylamide]hexane, and polymerizable compounds 1 to 12 described in paragraph [0031] of Journal of Technical Disclosure 2013-502654. These compounds may be used alone or in combination of two or more thereof.

Further, polyfunctional (meth)acrylates and polyfunctional (meth)acrylamides may be used in combination.

<Monofunctional (Meth)Acrylate and Monofunctional (Meth)Acrylamide>

Specific examples of the monofunctional (meth)acrylate include alkyl acrylates such as methyl acrylate, ethyl acrylate, propyl acrylate, butyl acrylate, isobutyl acrylate, amyl acrylate, hexyl acrylate, 2-ethylhexyl acrylate, octyl acrylate, benzyl acrylate, 2-chloroethyl acrylate, glycidyl acrylate, 3,4-epoxycyclohexylmethyl acrylate, vinyl acrylate, 2-phenylvinyl acrylate, 1-propenyl acrylate, allyl acrylate, 2-allyloxyethyl acrylate, and propargyl acrylate; and alkyl methacrylates such as methyl methacrylate, ethyl methacrylate, propyl methacrylate, butyl methacrylate, isobutyl methacrylate, lauryl methacrylate [hereinafter, also referred to simply as "LMA"], amyl methacrylate, hexyl methacrylate, 2-ethylhexyl methacrylate, cyclohexyl methacrylate, benzyl methacrylate, 2-chloroethyl methacrylate, glycidyl methacrylate, 3,4-epoxycyclohexylmethyl methacrylate, vinyl methacrylate, 2-phenylvinyl methacrylate, 1-propenyl methacrylate, allyl methacrylate, 2-allyloxyethyl methacrylate, and propargyl methacrylate. These compounds may be used alone or in combination of two or more thereof.

Specific examples of the monofunctional (meth)acrylamide include acrylamide, methacrylamide, N-methylol acrylamide, N-ethyl acrylamide, N-hexyl methacrylamide, N-cyclohexyl acrylamide, N-hydroxyethyl acrylamide, N-phenyl acrylamide, N-nitrophenyl acrylamide, N-ethyl-N-phenyl acrylamide, vinyl acrylamide, vinyl methacrylamide, N,N-diallyl acrylamide, N,N-diallyl methacrylamide, allyl acrylamide, allyl methacrylamide, and N-(2-acetamidoethyl)-N-(2-hydroxyethyl)acrylamide. These compounds may be used alone or in combination of two or more thereof.

Further, monofunctional (meth)acrylates and monofunctional (meth)acrylamides may be used in combination.

The polymerizable compound C other than the (meth)acrylic compounds exemplified above is preferably a polymerizable compound having a hydrophilic group, in terms of that antistatic properties become better due to high compatibility with the photopolymerization initiator A.

Examples of the hydrophilic group include a hydroxy group, a betaine group, and a carboxyl group. Among them, preferred is a hydroxy group or a betaine group, and more preferred is a hydroxy group.

The polymerizable compound having a hydroxy group is preferably a compound represented by the following Formula (9).

$$CH_2=C(R^{11})COO(BO)_nH \quad (9)$$

In Formula (9), $R^{11}$ represents a hydrogen atom or $CH_3$, B represents an alkylene group having 2 or 3 carbon atoms which may be branched, and n represents an integer of 1 to 10.

Specific examples of the compound represented by Formula (9) include 2-hydroxyethyl acrylate, 2-hydroxyethyl methacrylate [hereinafter, also referred to simply as "HEMA"], 2-hydroxypropyl acrylate, 3-hydroxypropyl acrylate, 4-hydroxybutyl acrylate, 2-hydroxypropyl methacrylate, 3-hydroxypropyl methacrylate, and 4-hydroxybutyl methacrylate. These compounds may be used alone or in combination of two or more thereof.

In the present invention, regarding the content of components in a case of containing the polymerizable compound C, it is preferred to contain 0.3 to 9 parts by mass of the photopolymerization initiator A, 1 to 30 parts by mass of the antistatic polymer B, and 69.7 to 90 parts by mass of the polymerizable compound C, and it is more preferred to contain 0.35 to 7 parts by mass of the photopolymerization initiator A, 3.5 to 22.5 parts by mass of the antistatic polymer B, and 77.15 to 89.5 parts by mass of the polymerizable compound C, with respect to 100 parts by mass of the total solid content contained in the composition.

The composition of the present invention may contain a solvent, if necessary.

Examples of the solvent to be used include water, an organic solvent and a mixed solvent thereof.

Specific examples of the organic solvent include alcohols such as methanol and isopropyl alcohol; ketones such as acetone; amides such as formamide; sulfoxides such as dimethyl sulfoxide; esters such as ethyl acetate; and ethers.

Depending on the intended use, the composition of the present invention may contain other optional components such as a pigment, a dye, a surfactant, an anti-blocking agent, a binder, a crosslinking agent, an antioxidant, and an ultraviolet absorber which may be used in combination.

[Antistatic Film]

The antistatic film of the present invention is an antistatic film which has an antistatic layer formed by applying the composition of the present invention onto a substrate, and curing the applied composition by active energy rays.

[Substrate]

The substrate in the antistatic film of the present invention is preferably a substrate formed of a material having good transparency. Specific examples of the material for a substrate include polyethylene terephthalate, polybutylene terephthalate, polyethylene, polypropylene, nylon 6, nylon 66, diacetyl cellulose, triacetyl cellulose, acetyl cellulose butyrate, cellophane, polystyrene, polyarylate, polycarbonate, polyvinyl chloride, polyvinylidene chloride, polymethyl terpene, polyether sulfone, polymethyl methacrylate, polyvinyl alcohol, polyimide, and polycycloolefin.

[Antistatic Layer]

The method of applying the composition of the present invention onto a substrate is not particularly limited, and example thereof include coating methods such as by a gravure coater, a comma coater, a bar coater, a knife coater, a die coater, and a roll coater.

After applying the composition of the present invention onto a substrate to form a coating film, a drying process may be carried out, if necessary, prior to carrying out a curing process to be described hereinafter. By carrying out the drying process, it is possible to remove volatile components (such as a solvent) contained in the coating film. The method of drying process is not particularly limited, and examples thereof include a method of carrying out a heat treatment at a temperature (for example, 60° C. to 100° C.) at which the polymerization of a polymerizable compound does not proceed, and a method of carrying out an air-drying process.

The method of applying the composition of the present invention onto a substrate to form a coating film and then curing the coating film by active energy rays is not particularly limited.

As used herein, the term "active energy rays" refers to energy rays capable of generating an active species by decomposing a compound (photopolymerization initiator A) which generates the active species. Examples of such active energy rays include light rays such as far ultraviolet rays, ultraviolet rays, near ultraviolet rays, and infrared rays; electromagnetic waves such as X-rays and γ-rays; an electron beams, proton beams, and neutron rays. From the viewpoint of a curing rate, easy availability of an irradiation device, and costs, ultraviolet rays are preferable.

UV irradiation can be carried out using a high-pressure mercury lamp, ultra-high pressure mercury lamp, carbon arc lamp, metal halide lamp, xenon lamp, chemical lamp, electrodeless discharge lamp, ultraviolet LED or the like which emits light of a 150 to 450 nm wavelength range.

Further, the illuminance of light irradiation performed on a coating film is not particularly limited, but it is preferably 0.1 to 1,000 $mW/cm^2$ and more preferably 1 to 800 $mW/cm^2$ from the viewpoint of the balance of properties and productivity of the resulting antistatic film.

The exposure dose at the time of light irradiation is not particularly limited, but it is preferably 2,000 $mJ/cm^2$ or less, more preferably 1,750 $mJ/cm^2$ or less, and still more preferably 1,500 $mJ/cm^2$ or less from the viewpoint of the balance of properties and productivity of the resulting antistatic film. The lower limit is not particularly limited, but it is preferably 500 $mJ/cm^2$ or more from the viewpoint of properties of an antistatic film.

The atmosphere at the time of light irradiation is not particularly limited and may be in the air or under an inert gas atmosphere.

The thickness of the antistatic layer formed using the composition of the present invention is preferably 0.01 to 100 μm and more preferably 0.05 to 50 μm.

The hardness of the antistatic layer is preferably HB or more and more preferably H or more, as determined by a pencil hardness test.

The common logarithmic value (Log SR) of the surface resistivity SR(Ω/sq) of the antistatic layer is preferably 13 or less and more preferably 12 or less.

Here, the surface resistivity represents a value measured at 25° C. and 60% relative humidity.

EXAMPLES

Hereinafter, the present invention will be described in more detail with reference to the following Examples. Materials, used amounts, ratios, processing contents, processing procedures and the like shown in the following Examples may be appropriately changed without departing from the scope and sprit of the present invention. Accordingly, the scope of the present invention should not be limitatively interpreted by the following Examples.

[Synthesis of Polymerization Initiator]

<Synthesis of Intermediate (2)-1>

97.2 g (0.95 mol) of an acetic anhydride was added dropwise to 170.0 g (0.93 mol) of phenyl diglycol (PhDG, manufactured by Nippon Nyukazai Co., Ltd.) heated to 90° C., followed by stirring under heating at 120° C. for 6 hours. Then, the reaction mixture was concentrated under reduced pressure to give 204.4 g (yield: 98%) of Intermediate (2)-1. The structure of the resulting Intermediate (2)-1 was determined using a nuclear magnetic resonance apparatus (solvent used: CDCl$_3$) and was therefore identified as a compound of the following Formula (2)-1. The measurement data of $^1$H-NMR is shown below.

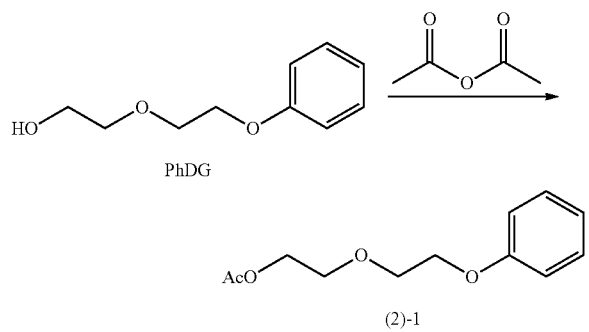

Scheme 1

(2)-1

$^1$H-NMR (CDCl$_3$)
δ: 2.10 (3H, s), 3.78 (2H, m), 3.87 (2H, m), 4.15 (2H, m), 4.26 (2H, m), 6.90-6.98 (3H, m), 7.25-7.32 (2H, m)

<Synthesis of Intermediate (3)-1>

120.0 g (0.90 mol) of aluminum chloride (III) was added to 270 mL (2.39 mol) of o-dichlorobenzene and the mixture was cooled to 0° C. 44.26 mL (0.36 mol) of 2-bromoisobutyryl bromide was added dropwise thereto, followed by stirring for 15 minutes. Thereafter, 67.28 g (0.30 mol) of Intermediate (2)-1 was added dropwise over 30 minutes, while maintaining the temperature of the reaction liquid at 0° C. The reaction liquid after the dropwise addition was allowed to return to room temperature (22° C.) and stirred for 2 hours. Then, the reaction liquid was added in several divided portions to 300 mL of water cooled to 5° C. The organic phase was washed twice with 300 mL of water, 135 mL of sodium bicarbonate water, and then 135 mL of saturated saline. 300 mL of water was added to the organic phase, followed by azeotropic concentration under reduced pressure to give 110.8 g (yield: 95%) of Intermediate (3)-1. The structure of the resulting Intermediate (3)-1 was determined using a nuclear magnetic resonance apparatus (solvent used: CDCl$_3$) and was therefore identified as a compound of the following Formula (3)-1. The measurement data of $^1$H-NMR is shown below.

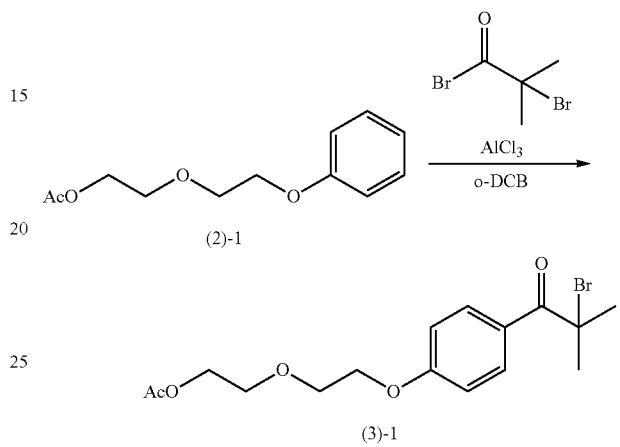

Scheme 2

(2)-1

(3)-1

$^1$H-NMR (CDCl$_3$)
δ: 2.04 (6H, s), 2.08 (3H, s), 3.79 (2H, m), 3.85 (2H, m), 4.21 (2H, m), 4.26 (2H, 6.94 (2H, d), 8.21 (2H, d)

<Synthesis of Photopolymerization Initiator A: Compound (I)-1>

100.0 g (0.27 mol) of Compound (3)-1 was dissolved in 200 mL of isopropyl alcohol to which 214 g of a 25 mass % sodium hydroxide aqueous solution was then added dropwise, followed by stirring for 2 hours. Thereafter, stirring was stopped, and the organic phase was washed twice with saturated saline and then neutralized with hydrochloric acid. The organic phase was concentrated under reduced pressure, 72 mL of methyl ethyl ketone was added thereto, and the precipitated salt was filtered. After the filtrate was concentrated under reduced pressure, 72 mL of water was added, and azeotropic concentration under reduced pressure was carried out to give 56.8 g (yield: 87%) of Compound (I)-1.

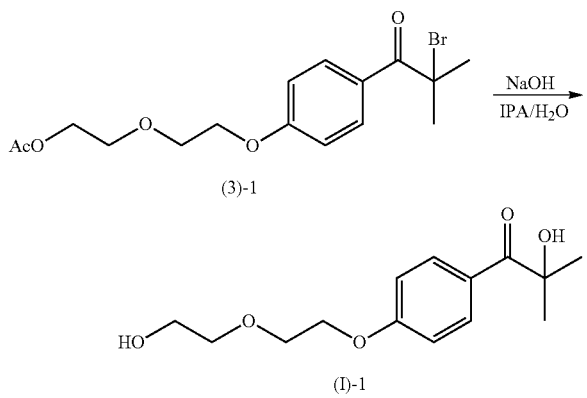

Scheme 3

(3)-1

(I)-1

$^1$H-NMR (CDCl$_3$)
δ: 1.64 (6H, s), 3.69 (2H, m), 3.78 (2H, m), 3.91 (2H, m), 4.22 (2H, m), 4.26 (1H, s), 6.97 (2H, d), 8.06 (2H, d)

[Synthesis of Other Photopolymerization Initiators]

As the compound represented by Formula (1), a compound represented by the following Formula (I)-2, a compound represented by the following Formula (I)-4, and a compound represented by Formula (IB) were synthesized with reference to the above-mentioned procedure.

Further, as shown in Table 13 to be described hereinafter, a commercially available product "Irgacure 2959" (Irg2959) (trade name, manufactured by BASF Corporation) was used as the compound used in Comparative Examples. As shown in the following formula, Irg2959 corresponds to a compound of n=0 in Formula (I).

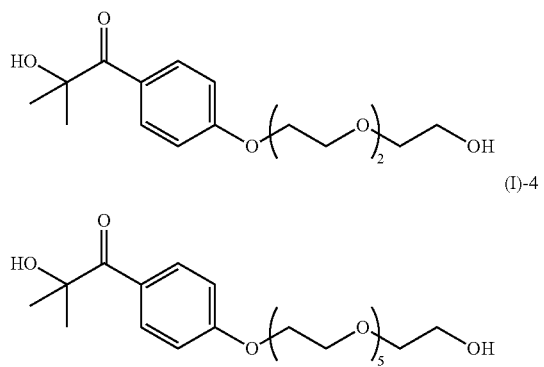

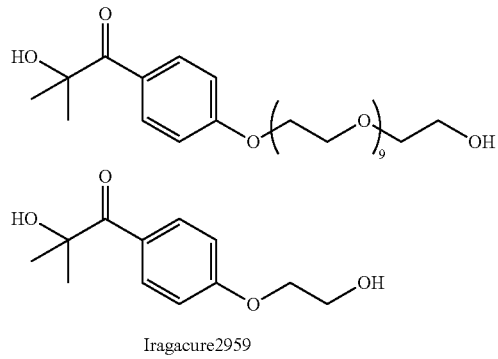

Iragacure2959

[Synthesis of Antistatic Polymer B]

Synthesis Examples 1 to 49

In a flask equipped with stirring blades, a reflux condenser and a gas inlet, a monomer, a polymerization initiator (azobisisobutyronitrile (AIBN)) and a solvent (isopropyl alcohol (IPA)) shown in the following Tables 2 to 6 were mixed in an amount (parts by mass) shown in Tables 2 to 6, and reacted for 8 hours at 70° C. under a nitrogen atmosphere, thereby synthesizing Polymer B.

TABLE 2

| Synthesis of Polymer B | | 1 | 2 | 3 | 4 | 5 | 6 | 7 | 8 | 9 | 10 | 11 | 12 |
|---|---|---|---|---|---|---|---|---|---|---|---|---|---|
| Monomer | (B)-a1-1 | 100 | 80 | 40 | 60 | 59.5 | 50 | 59 | | | | | |
| | (B)-a1-2 | | | | | | | | 100 | 80 | 40 | 60 | 59.5 |
| | (B)-a1-3 | | | | | | | | | | | | |
| | (B)-a1-4 | | | | | | | | | | | | |
| | (B)-a1-5 | | | | | | | | | | | | |
| | (B)-a1-6 | | | | | | | | | | | | |
| | (B)-a1-7 | | | | | | | | | | | | |
| | (B)-a1-8 | | | | | | | | | | | | |
| | (B)-a1-9 | | | | | | | | | | | | |
| | (B)-a1-10 | | | | | | | | | | | | |
| | (B)-a1-11 | | | | | | | | | | | | |
| | (B)-b-1 | | 20 | 60 | 40 | 40 | 40 | 40 | | 20 | 60 | 40 | 40 |
| | (B)-a3-1 | | | | | 0.5 | 10 | 1 | | | | | 0.5 |
| | (B)-d-1 CLogP: 2.384 | | | | | | | | | | | | |
| | (B)-d-10 CLogP: 0.3032 | | | | | | | | | | | | |
| | (B)-d-7 CLogP: 4.37 | | | | | | | | | | | | |
| Polymerization initiator | AIBN | 0.5 | 0.5 | 0.5 | 0.5 | 0.5 | 0.5 | 0.5 | 0.5 | 0.5 | 0.5 | 0.5 | 0.5 |
| Solvent | IPA | 300 | 300 | 300 | 300 | 300 | 300 | 300 | 300 | 300 | 300 | 300 | 300 |

| Synthesis of Polymer B | | 13 | 14 | 15 | 16 | 17 | 18 | 19 | 20 | 21 | 22 | 23 |
|---|---|---|---|---|---|---|---|---|---|---|---|---|
| Monomer | (B)-a1-1 | | | | | | | | | | | |
| | (B)-a1-2 | 50 | 59 | | | | | | | | | |
| | (B)-a1-3 | | | 100 | 80 | 40 | 60 | 59.5 | 50 | 59 | | |
| | (B)-a1-4 | | | | | | | | | | 100 | 59 |
| | (B)-a1-5 | | | | | | | | | | | |
| | (B)-a1-6 | | | | | | | | | | | |
| | (B)-a1-7 | | | | | | | | | | | |
| | (B)-a1-8 | | | | | | | | | | | |
| | (B)-a1-9 | | | | | | | | | | | |
| | (B)-a1-10 | | | | | | | | | | | |

TABLE 2-continued

| | | | | | | | | | | | | |
|---|---|---|---|---|---|---|---|---|---|---|---|---|
| | (B)-a1-11 | | | | | | | | | | | |
| | (B)-b-1 | 40 | 40 | | 20 | 60 | 40 | 40 | 40 | 40 | | 40 |
| | (B)-a3-1 | 10 | 1 | | | | | | 0.5 | 10 | 1 | 1 |
| | (B)-d-1 CLogP: 2.384 | | | | | | | | | | | |
| | (B)-d-10 CLogP: 0.3032 | | | | | | | | | | | |
| | (B)-d-7 CLogP: 4.37 | | | | | | | | | | | |
| Polymerization initiator | AIBN | 0.5 | 0.5 | 0.5 | 0.5 | 0.5 | 0.5 | 0.5 | 0.5 | 0.5 | 0.5 | 0.5 |
| Solvent | IPA | 300 | 300 | 300 | 300 | 300 | 300 | 300 | 300 | 300 | 300 | 300 |

TABLE 3

| | | Synthesis Examples | | | | | | | |
|---|---|---|---|---|---|---|---|---|---|
| Synthesis of Polymer B | | 24 | 25 | 26 | 27 | 28 | 29 | 30 | 31 |
| Monomer | (B)-a1-1 | | | | | | | | |
| | (B)-a1-2 | | | | | | | | |
| | (B)-a1-3 | | | | | | | | |
| | (B)-a1-4 | | | | | | | | |
| | (B)-a1-5 | 100 | 59 | | | | | | |
| | (B)-a1-6 | | | 100 | 59 | | | | |
| | (B)-a1-7 | | | | | 100 | 59 | | |
| | (B)-a1-8 | | | | | | | 100 | 59 |
| | (B)-a1-9 | | | | | | | | |
| | (B)-a1-10 | | | | | | | | |
| | (B)-a1-11 | | | | | | | | |
| | (B)-b-1 | | 40 | | 40 | | 40 | | 40 |
| | (B)-a3-1 | | 1 | | 1 | | 1 | | 1 |
| | (B)-d-1 CLogP: 2.384 | | | | | | | | |
| | (B)-d-10 CLogP: 0.3032 | | | | | | | | |
| | (B)-d-7 CLogP: 4.37 | | | | | | | | |
| Polymerization initiator | AIBN | 0.5 | 0.5 | 0.5 | 0.5 | 0.5 | 0.5 | 0.5 | 0.5 |
| Solvent | IPA | 300 | 300 | 300 | 300 | 300 | 300 | 300 | 300 |

TABLE 4

| | | Synthesis Examples | | | | | | | | | | | |
|---|---|---|---|---|---|---|---|---|---|---|---|---|---|
| Synthesis of Polymer B | | 32 | 33 | 34 | 35 | 36 | 37 | 38 | 39 | 40 | 41 | 42 | 43 |
| Monomer | (B)-a1-1 | | | | | | | 59 | 59 | 59 | | | |
| | (B)-a1-2 | | | | | | | | | | 59 | 59 | 59 |
| | (B)-a1-3 | | | | | | | | | | | | |
| | (B)-a1-4 | | | | | | | | | | | | |
| | (B)-a1-5 | | | | | | | | | | | | |
| | (B)-a1-6 | | | | | | | | | | | | |
| | (B)-a1-7 | | | | | | | | | | | | |
| | (B)-a1-8 | | | | | | | | | | | | |
| | (B)-a1-9 | 100 | 59 | | | | | | | | | | |
| | (B)-a1-10 | | | 100 | 59 | | | | | | | | |
| | (B)-a1-11 | | | | | 100 | 59 | | | | | | |
| | (B)-b-1 | | 40 | | 40 | | 40 | 20 | 20 | 20 | 20 | 20 | 20 |
| | (B)-a3-1 | | 1 | | 1 | | 1 | 1 | 1 | 1 | 1 | 1 | 1 |
| | (B)-d-1 CLogP: 2.384 | | | | | | | | | | 20 | | 20 |
| | (B)-d-10 CLogP: 0.3032 | | | | | | | | 20 | | | 20 | |
| | (B)-d-7 CLogP: 4.37 | | | | | | | | | 20 | | | 20 |
| Polymerization initiator | AIBN | 0.5 | 0.5 | 0.5 | 0.5 | 0.5 | 0.5 | 0.5 | 0.5 | 0.5 | 0.5 | 0.5 | 0.5 |
| Solvent | IPA | 300 | 300 | 300 | 300 | 300 | 300 | 300 | 300 | 300 | 300 | 300 | 300 |

TABLE 5

| Synthesis of Polymer B | | Synthesis Examples | | |
|---|---|---|---|---|
| | | 44 | 45 | 46 |
| Monomer | (B)-a2-1 | 60 | | |
| | (B)-a2-2 | | 60 | |
| | (B)-a2-3 | | | 60 |
| | (B)-b-1 | 40 | 40 | 40 |
| Polymerization initiator | AIBN | 0.5 | 0.5 | 0.5 |
| Solvent | IPA | 300 | 300 | 300 |

TABLE 6

| Synthesis of Polymer B | | Synthesis Examples | | |
|---|---|---|---|---|
| | | 47 | 48 | 49 |
| Monomer | (B)-a3-3 | 60 | | |
| | (B)-a4-1 | | 60 | |
| | (B)-a5-1 | | | 60 |
| | (B)-b-1 | 40 | 40 | 40 |
| Polymerization initiator | AIBN | 0.5 | 0.5 | 0.5 |
| Solvent | IPA | 300 | 300 | 300 |

Examples 1 to 58 and Comparative Examples 1 to 5

(Preparation of Active Energy Ray-Curable Composition)

The components shown in Tables 7 to 13 were mixed in amounts (parts by mass) shown in Tables 7 to 13 and stirred to obtain compositions.

In Table 10, polymerizable compounds shown below were respectively used as Compounds C1 to C3.

Compound 1: Difunctional urethane acrylate oligomer (manufactured by Shin-Nakamura Chemical Co., Ltd.: UA-4400, weight-average molecular weight: about 1,300 to 1,400)

Compound 2: Difunctional urethane acrylate oligomer (manufactured by Kyoeisha Chemical Co., Ltd.: UF-8001G, weight-average molecular weight: about 4,500)

Compound 3: Compound represented by the following formula

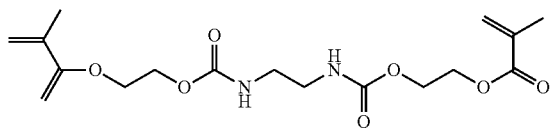 [SMILES: C=C(C)C(=C)OCCOC(=O)NCCNC(=O)OCCOC(=O)C(=C)C]

<Preparation of Antistatic Film>

Each of the prepared compositions was applied onto a polyethylene terephthalate film (Cosmo Shine A4100 manufactured by Toyobo Co., Ltd.) using a bar coater, the solvent was removed in a hot air oven, ultraviolet rays were irradiated for 10 seconds by a high-pressure mercury lamp having an output of 80 w/cm, and the coating layer (thickness: 5 µm) was cured to prepare an antistatic film.

The thus-prepared antistatic film was cut into a size of width 100 mm×length 100 mm with a cutter and the resulting sample was evaluated according to the following evaluation method. The results are shown in Tables 7 to 13 below.

(Antistatic Properties)

The antistatic properties were evaluated by allowing the cut sample to stand for 24 hours under an atmosphere of 25° C. and 40% relative humidity, and applying an applied voltage of 100 V to the sample under conditions of 25° C. and 40% relative humidity and then measuring surface resistivity (Ω/□) after 1 minute using a surface electrical resistance meter (SME-8310, Toa Electronics Co., Ltd).

In addition, the antistatic properties under low humidity were evaluated by allowing the sample to stand for 24 hours under an atmosphere of 25° C. and 15% relative humidity and measuring surface resistivity (Ω/□) in the same manner as described above.

The antistatic properties were evaluated on a 6-point scale according to the following evaluation standards. The article with a grade of D or higher can be used without any practical problem.

A: Superior (surface electrical resistance value of less than $10^9$ Ω/area)

B: Excellent (surface electrical resistance value of $10^9$ Ω/area or more and less than $10^{10}$ Ω/area)

C: Good (surface electrical resistance value of $10^{10}$ Ω/area or more and less than $10^{11}$ Ω/area)

D: Moderate (surface electrical resistance value of $10^{11}$ Ω/area or more and less than $10^{12}$ Ω/area)

E: Slightly bad (surface electrical resistance value of $10^{12}$ Ω/area or more and less than $10^{13}$ Ω/area)

F: Bad (surface electrical resistance value of $10^{13}$ Ω/area or more)

(Variation in Antistatic Properties after Thermocycles)

After carrying out a thermocycle test of 20 cycles each consisting of temperature changes (20° C. for 50 hours under 45% relative humidity atmosphere→−20° C. for 50 hours under 20% relative humidity atmosphere→50° C. for 50 hours under 85% relative humidity atmosphere) as one cycle, the surface resistivity (Ω/□) was measured in the same manner as described above. From the values of surface resistivity before and after the thermocycle test, a variation was calculated according to the following equation.

Variation=(surface electrical resistance value after test)/(surface electrical resistance value before test)

(Scratch Resistance)

The presence or absence of occurrence of scratches on the surface was evaluated by reciprocating #0000 steel wool under a load of 200 g/cm² 10 times on the entire surface of the layer having an antistatic film.

A: No scratch is visible even with very careful watching.

B: Slightly weak scratch is visible with very careful watching.

C: Weak scratch is visible on part of sample.

D: Streaky scratch is found over entire surface of coating film.

E: Peeling of coating film occurs.

(Transparency)

The transparency was evaluated in terms of haze (%). The measurement of haze was carried out using a haze meter "NDH 5000" manufactured by Nippon Denshoku Industries Co., Ltd., after 3-week storage of individual antistatic films obtained in Examples and Comparative Examples under the condition of −20° C. In addition, a polyethylene terephthalate film having no antistatic film was subjected to the same measurement and taken as blank.

A: Less than 0.5%

B: 0.5% or more

TABLE 7

| | | Examples | | | | | | | | | | | |
|---|---|---|---|---|---|---|---|---|---|---|---|---|---|
| | | 1 | 2 | 3 | 4 | 5 | 6 | 7 | 8 | 9 | 10 | 11 | 12 |
| Polymer B | Synthesis Example No. | 1 | 2 | 3 | 4 | 5 | 6 | 7 | 8 | 9 | 10 | 11 | 12 |
| | Blending amount | 20 | 20 | 20 | 20 | 20 | 20 | 20 | 20 | 20 | 20 | 20 | 20 |
| Photopolymerization initiator A | (1)-1 | 5 | 5 | 5 | 5 | 5 | 5 | 5 | 5 | 5 | 5 | 5 | 5 |
| | (1)-2 | | | | | | | | | | | | |
| | (1)-4 | | | | | | | | | | | | |
| Polymerizable compound C | DPHA | 100 | 100 | 100 | 100 | 100 | 100 | 100 | 100 | 100 | 100 | 100 | 100 |
| Solvent | IPA | 105 | 105 | 105 | 105 | 105 | 105 | 105 | 105 | 105 | 105 | 105 | 105 |
| Antistatic properties | | A | A | A | A | A | A | A | A | A | A | A | A |
| Antistatic properties under low humidity | | C | C | C | C | C | B | B | C | C | C | C | C |
| Variation in antistatic properties after thermocycle | | 1.27 | 1.24 | 1.23 | 1.22 | 1.15 | 1.18 | 1.11 | 1.29 | 1.26 | 1.24 | 1.22 | 1.16 |
| Scratch resistance | | B | B | B | B | B | B | B | B | B | B | B | B |
| Transparency | | A | A | A | A | A | A | A | A | A | A | A | A |

| | | Examples | | | | | | | | | | |
|---|---|---|---|---|---|---|---|---|---|---|---|---|
| | | 13 | 14 | 15 | 16 | 17 | 18 | 19 | 20 | 21 | 22 | 23 |
| Polymer B | Synthesis Example No. | 13 | 14 | 15 | 16 | 17 | 18 | 19 | 20 | 21 | 22 | 23 |
| | Blending amount | 20 | 20 | 20 | 20 | 20 | 20 | 20 | 20 | 20 | 20 | 20 |
| Photopolymerization initiator A | (1)-1 | 5 | 5 | 5 | 5 | 5 | 5 | 5 | 5 | 5 | 5 | 5 |
| | (1)-2 | | | | | | | | | | | |
| | (1)-4 | | | | | | | | | | | |
| Polymerizable compound C | DPHA | 100 | 100 | 100 | 100 | 100 | 100 | 100 | 100 | 100 | 100 | 100 |
| Solvent | IPA | 105 | 105 | 105 | 105 | 105 | 105 | 105 | 105 | 105 | 105 | 105 |
| Antistatic properties | | A | A | A | A | A | A | A | A | A | A | A |
| Antistatic properties under low humidity | | B | B | C | C | C | C | C | B | B | C | B |
| Variation in antistatic properties after thermocycle | | 1.2 | 1.12 | 1.3 | 1.25 | 1.24 | 1.22 | 1.18 | 1.2 | 1.13 | 1.27 | 1.12 |
| Scratch resistance | | B | B | B | B | B | B | B | B | B | B | B |
| Transparency | | A | A | A | A | A | A | A | A | A | A | A |

TABLE 8

| | | Examples | | | | | | | |
|---|---|---|---|---|---|---|---|---|---|
| | | 24 | 25 | 26 | 27 | 28 | 29 | 30 | 31 |
| Polymer B | Synthesis Example No. | 24 | 25 | 26 | 27 | 28 | 29 | 30 | 31 |
| | Blending amount | 20 | 20 | 20 | 20 | 20 | 20 | 20 | 20 |
| Photopolymerization initiator A | (1)-1 | 5 | 5 | 5 | 5 | 5 | 5 | 5 | 5 |
| | (1)-2 | | | | | | | | |
| | (1)-4 | | | | | | | | |
| Polymerizable compound C | DPHA | 100 | 100 | 100 | 100 | 100 | 100 | 100 | 100 |
| Solvent | IPA | 105 | 105 | 105 | 105 | 105 | 105 | 105 | 105 |
| Antistatic properties | | A | A | A | A | A | A | A | A |
| Antistatic properties under low humidity | | C | B | C | B | C | B | C | B |
| Variation in antistatic properties after thermocycle | | 1.28 | 1.15 | 1.3 | 1.16 | 1.31 | 1.16 | 1.3 | 1.16 |
| Scratch resistance | | B | B | B | B | B | B | B | B |
| Transparency | | A | A | A | A | A | A | A | A |

TABLE 9

| | | Examples | | | | | | | | |
|---|---|---|---|---|---|---|---|---|---|---|
| | | 32 | 33 | 34 | 35 | 36 | 37 | 38 | 39 | 40 |
| Polymer B | Synthesis Example No. | 32 | 33 | 34 | 35 | 36 | 37 | 38 | 39 | 40 |
| | Blending amount | 20 | 20 | 20 | 20 | 20 | 20 | 20 | 20 | 20 |

TABLE 9-continued

| | | | | | | | | | | |
|---|---|---|---|---|---|---|---|---|---|---|
| Photopolymerization initiator A | (1)-1 | 5 | 5 | 5 | 5 | 5 | 5 | 5 | 5 | 5 |
| | (1)-2 | | | | | | | | | |
| | (1)-4 | | | | | | | | | |
| Polymerizable compound C | DPHA | 100 | 100 | 100 | 100 | 100 | 100 | 100 | 100 | 100 |
| Solvent | IPA | 105 | 105 | 105 | 105 | 105 | 105 | 105 | 105 | 105 |
| Antistatic properties | | A | A | B | B | B | B | A | A | A |
| Antistatic properties under low humidity | | C | B | C | C | C | C | B | B | B |
| Variation in antistatic properties after thermocycle | | 1.36 | 1.19 | 1.56 | 1.26 | 1.55 | 1.29 | 1.08 | 1.09 | 1.07 |
| Scratch resistance | | B | B | B | B | B | B | B | B | B |
| Transparency | | A | A | A | A | A | A | A | A | A |

| | | Examples | | | | | | | | |
|---|---|---|---|---|---|---|---|---|---|---|
| | | 41 | 42 | 43 | 44 | 45 | 46 | 47 | 48 | 49 |
| Polymer B | Synthesis Example No. | 41 | 42 | 43 | 1 | 1 | 1 | 1 | 1 | 1 |
| | Blending amount | 20 | 20 | 20 | 20 | 20 | 20 | 20 | 1 | 40 |
| Photopolymerization initiator A | (1)-1 | 5 | 5 | 5 | 1 | 10 | | | 5 | 5 |
| | (1)-2 | | | | | | 5 | | | |
| | (1)-4 | | | | | | | 5 | | |
| Polymerizable compound C | DPHA | 100 | 100 | 100 | 100 | 100 | 100 | 100 | 100 | 100 |
| Solvent | IPA | 105 | 105 | 105 | 105 | 105 | 105 | 105 | 105 | 105 |
| Antistatic properties | | A | A | A | B | A | B | B | C | A |
| Antistatic properties under low humidity | | B | B | B | D | C | C | D | D | C |
| Variation in antistatic properties after thermocycle | | 1.09 | 1.1 | 1.08 | 1.36 | 0.69 | 0.71 | 0.67 | 1.56 | 1.3 |
| Scratch resistance | | B | B | B | C | C | B | C | A | C |
| Transparency | | A | A | A | A | A | A | A | A | A |

TABLE 10

| | | Examples | | |
|---|---|---|---|---|
| | | 50 | 51 | 52 |
| Polymer B | Synthesis Example No. | 44 | 45 | 46 |
| | Blending amount | 20 | 20 | 20 |
| Photopolymerization initiator A | (I)-1 | 5 | 5 | 5 |
| Polymerizable compound C | DPHA | 100 | 100 | 100 |
| Solvent | IPA | 105 | 105 | 105 |
| Antistatic properties | | C | C | C |
| Antistatic properties under low humidity | | C | C | C |
| Variation in antistatic properties after thermocycle | | 1.45 | 1.46 | 1.47 |
| Scratch resistance | | C | C | C |
| Transparency | | A | A | A |

TABLE 11

| | | Examples | | |
|---|---|---|---|---|
| | | 53 | 54 | 55 |
| Polymer B | Synthesis Example No. | 47 | 48 | 49 |
| | Blending amount | 20 | 20 | 20 |
| Photopolymerization initiator A | (I)-1 | 5 | 5 | 5 |
| Polymerizable compound C | DPHA | 100 | 100 | 100 |
| Solvent | IPA | 105 | 105 | 105 |
| Antistatic properties | | B | B | B |
| Antistatic properties under low humidity | | C | C | C |
| Variation in antistatic properties after thermocycle | | 1.44 | 1.44 | 1.45 |
| Scratch resistance | | B | B | B |
| Transparency | | A | A | A |

TABLE 12

|  |  | Examples | | |
|---|---|---|---|---|
|  |  | 56 | 57 | 58 |
| Polymer B | Synthesis Example No. | 1 | 1 | 1 |
|  | Blending amount | 20 | 20 | 20 |
| Photopolymerization initiator A | (I)-1 | 5 | 5 | 5 |
| Polymerizable compound C | Compound C1 | 100 |  |  |
|  | Compound C2 |  | 100 |  |
|  | Compound C3 |  |  | 100 |
| Solvent | IPA | 105 | 105 | 105 |
| Antistatic properties |  | B | B | B |
| Antistatic properties under low humidity |  | C | D | C |
| Variation in antistatic properties after thermocycle |  | 1.29 | 1.31 | 0.68 |
| Scratch resistance |  | A | A | A |
| Transparency |  | A | A | A |

TABLE 13

|  |  | Comparative Examples | | | | |
|---|---|---|---|---|---|---|
|  |  | 1 | 2 | 3 | 4 | 5 |
| Polymer B | Synthesis Example No. | 1 | 7 | 1 | 7 | 1 |
|  | Blending amount | 20 | 20 | 20 | 20 | 20 |
| Photopolymerization initiator | Irgacure 2959 (IB) | 5 | 5 |  |  | 1 |
|  |  |  |  | 5 | 5 |  |
| Polymerizable compound C | DPHA | 100 | 100 | 100 | 100 | 100 |
| Solvent | IPA | 105 | 105 | 105 | 105 | 105 |
| Antistatic properties |  | D | D | C | C | D |
| Antistatic properties under low humidity |  | F | F | D | C | F |
| Variation in antistatic properties after thermocycle |  | 100> | 10> | 0.62 | 0.75 | 10> |
| Scratch resistance |  | E | E | D | D | E |
| Transparency |  | B | B | A | A | A |

From the results shown in Table 13, it was found that antistatic properties and scratch resistance were poor even when the blending amount and the polymer used in combination were changed (Comparative Examples 1, 2 and 5), in a case where a commercially available product (Irg2959 manufactured by BASF Corporation) is used as the photopolymerization initiator.

Further, it was found that antistatic properties were improved, but scratch resistance was poor (Comparative Examples 3 and 4), in a case where an initiator in which n in Formula (I) corresponds to 9 was used as the photopolymerization initiator.

In contrast, as shown in Tables 7 to 12, it was found that all of antistatic properties, scratch resistance, and transparency after curing become good (Examples 1 to 58), when a photopolymerization initiator A, an antistatic polymer B and a polymerizable compound C were blended.

Further, from the comparison of the results shown in Tables 7 to 12, it was found that antistatic properties and scratch resistance tended to become better when the antistatic polymer B was a cationic polymer represented by Formula (1).

Further, from the comparison of Examples 1, 46 and 47, it was found that antistatic properties and scratch resistance tended to become better when a photopolymerization initiator in which n in Formula (I) is 1 was used as the photopolymerization initiator A.

Further, from the comparison of Examples 1 to 7, and the comparison of Examples 24 and 25, it was found that antistatic properties, in particular, antistatic properties after a thermocycle test become better when the antistatic polymer B has a repeating unit represented by Formula (7) together with a repeating unit represented by Formula (1), and it was specially found that antistatic properties, in particular, antistatic properties under low humidity become better when the antistatic polymer B has a repeating unit represented by Formula (7) and a repeating unit represented by Formula (3) together with a repeating unit represented by Formula (1).

Further, from the comparison of Example 7 with Examples 38 to 40, it was found that antistatic properties, in particular, antistatic properties after a thermocycle test become better when the antistatic polymer B has a repeating unit derived from a monomer having a CLogP value of 0.3 to 5, together with a repeating unit represented by Formula (1).

What is claimed is:

1. An active energy ray-curable composition, comprising:
    a photopolymerization initiator A represented by the following Formula (I);
    an antistatic polymer B; and
    a polymerizable compound C containing an ethylenically unsaturated group,

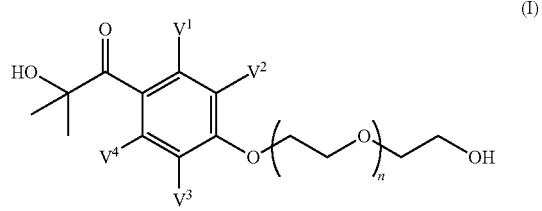

(I)

in Formula (I), $V^1$, $V^2$, $V^3$, and $V^4$ each independently represent a hydrogen atom or a substituent, and n represents an integer of 1 to 5, and wherein the antistatic polymer B is a polymer having at least one repeating unit selected from the group consisting of repeating units represented by the following Formulae (1) to (5),

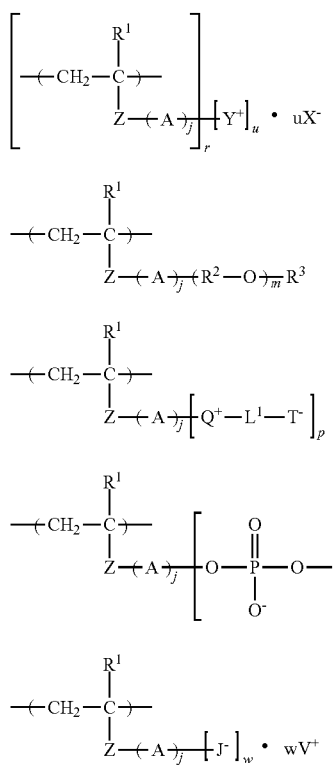

(1)

(2)

(3)

(4)

(5)

in Formulae (1) to (5), $R^1$'s each independently represent a hydrogen atom, a halogen atom, a cyano group, a monovalent hydrocarbon group, —COO—$C_2$, or —COO—$C_2$ bonded through a hydrocarbon, and $C_2$ represents a hydrogen atom or a hydrocarbon group which may have a substituent, in Formulae (1) to (5), Z's each independently represent —COO—, —CONH—, —OCO—, —CH$_2$OCO—, —CH$_2$COO—, —O—, —SO$_2$—, —CO—, —CONHCOO—, —CONHCONH—, —CONHSO$_2$—, —CON(P$_3$)—, —SO$_2$N(G)-, —C$_6$H$_4$—, or an alkylene group having 1 to 30 carbon atoms, and G represents a hydrogen atom or a hydrocarbon group, in Formulae (1) to (5), A's each independently represent a single bond or a divalent or higher valent linking group, and j's each independently represent an integer of 0 to 30, in Formula (1), $Y^+$ represents a cationic group, $X^-$ represents an anionic group, u represents an integer of 1 to 3, and r represents an integer of 1 to 4, in Formula (2), $R^2$ represents an alkylene group having 2 to 5 carbon atoms which may have a substituent, $R^3$ represents a hydrogen atom or an alkyl group having 1 to 5 carbon atoms which may have a substituent, and m represents an integer of 2 to 200, in Formula (3), $Q^+$ represents an ammonium cation, a sulfonium cation, an iodonium cation, a phosphonium cation, or a pyridinium cation, $L^1$ represents a single bond or a divalent or higher valent linking group, $T^-$ represents COO$^-$, SO$_3^-$ or OPO(O$^-$)(ORp), and Rp represents an alkyl group, and p represents an integer of 1 to 3, in Formula (4), $L^2$ represents a single bond or a divalent or higher valent linking group, $U^+$ represents an ammonium or phosphonium cation which may have a substituent, and q represents an integer of 1 to 3, and in Formula (5), $J^-$ represents COO$^-$, OPO(OH)O$^-$ or SO$_3^-$, $V^+$ represents a cationic group, and w represents an integer of 1 to 3.

2. The active energy ray-curable composition according to claim 1, wherein the antistatic polymer B is a cationic polymer having a repeating unit represented by Formula (1).

3. The active energy ray-curable composition according to claim 1, wherein the repeating unit represented by Formula (1) is an ammonium salt represented by the following Formula (6),

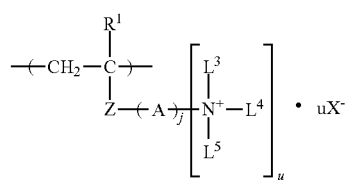

(6)

in Formula (6), $R^1$ represents a hydrogen atom, a halogen atom, a cyano group, a monovalent hydrocarbon group, —COO—$C_2$, or —COO—$C_2$ bonded through a hydrocarbon, and $C_2$ represents a hydrogen atom or a hydrocarbon group which may have a substituent, Z represents, —COO—, —CONH—, or —CH$_2$—, A represents a single bond or a divalent or higher valent linking group, and j represents an integer of 0 to 10, and $L^3$, $L^4$, and $L^5$ each independently represent an alkyl group, alkenyl group, alkynyl group, aryl group or heterocyclic group having 1 to 20 carbon atoms which may have a substituent, and at least two of $L^3$, $L^4$, and $L^5$ may be bonded to each other to form a ring.

4. The active energy ray-curable composition according to claim 1, wherein the antistatic polymer B contains at least one repeating unit selected from the group consisting of repeating units represented by Formulae (1) to (5) and a repeating unit represented by the following Formula (7),

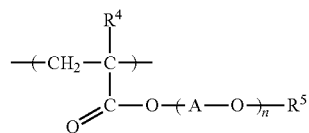

(7)

in Formula (7), $R^4$ represents a hydrogen atom or CH$_3$, $R^5$ represents a hydrogen atom or a hydrocarbon group having 6 to 25 carbon atoms which may have a substituent, A represents an alkylene group having 2 to 5 carbon atoms which may have a substituent, and n represents an integer of 3 to 50.

5. The active energy ray-curable composition according to claim 1, wherein the antistatic polymer B contains a repeating unit represented by Formula (1) and a repeating unit represented by Formula (3) or (4).

6. The active energy ray-curable composition according to claim 5, wherein the repeating unit represented by Formula (3) is a repeating unit represented by the following Formula (8),

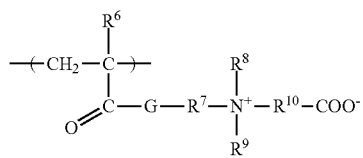
(8)

in Formula (8), $R^6$ represents a hydrogen atom or $CH_3$, $R^7$ represents an alkylene group having 1 to 6 carbon atoms, $R^8$ and $R^9$ each independently represent an alkyl group having 1 to 4 carbon atoms, and $R^{10}$ represents an alkylene group having 1 to 4 carbon atoms.

7. The active energy ray-curable composition according to claim 1, wherein the antistatic polymer B contains at least one repeating unit selected from the group consisting of repeating units represented by Formulae (1) to (5) and a repeating unit derived from a monomer having a CLogP value of 0.3 to 5.

8. The active energy ray-curable composition according to claim 1, wherein the antistatic polymer B is a copolymer containing 40 to 80 mass % of repeating units represented by Formulae (1) to (5).

9. The active energy ray-curable composition according to claim 8, wherein the antistatic polymer B contains 40 to 80 mass % of repeating units represented by Formulae (1) to (5), and 20 to 60 mass % of a repeating unit represented by Formula (7).

10. The active energy ray-curable composition according to claim 8, wherein the antistatic polymer B contains 39.5 to 70 mass % of a repeating unit represented by Formula (1), 20 to 60 mass % of a repeating unit represented by Formula (7), and 0.5 to 10 mass % of a repeating unit represented by Formula (3) or (4).

11. The active energy ray-curable composition according to claim 1, wherein the polymerizable compound C is a methacrylic or acrylic compound.

12. The active energy ray-curable composition according to claim 1, wherein the molecular weight of the polymerizable compound C is 90 to 5,000.

13. The active energy ray-curable composition according to claim 1, wherein the content of the photopolymerization initiator A is 0.5 to 10 parts by mass with respect to 100 parts by mass of the polymerizable compound C.

14. The active energy ray-curable composition according to claim 1, wherein the content of the polymer B is 1 to 40 parts by mass with respect to 100 parts by mass of the polymerizable compound C.

15. The active energy ray-curable composition according to claim 1, wherein the photopolymerization initiator A has n of 1 in Formula (I).

16. The active energy ray-curable composition according to claim 1, which is used in an antistatic agent.

17. An antistatic film comprising an antistatic layer formed by applying the active energy ray-curable composition according to claim 1 onto a substrate and curing the applied composition by active energy rays.

18. The active energy ray-curable composition according to claim 1, wherein the content of the polymer B is 5 to 30 parts by mass with respect to 100 parts by mass of the polymerizable compound C.

* * * * *